(12) United States Patent
Andrews et al.

(10) Patent No.: US 10,485,891 B2
(45) Date of Patent: Nov. 26, 2019

(54) MULTI-FUNCTION DRESSING STRUCTURE FOR NEGATIVE-PRESSURE THERAPY

(71) Applicant: KCI Licensing, Inc., San Antonio, TX (US)

(72) Inventors: Brian Andrews, Wimborne (GB); Timothy Mark Robinson, Basingstoke (GB); Christopher Brian Locke, Bournemouth (GB); David George Whyte, Wareham (GB)

(73) Assignee: KCI Licensing, Inc., San Antonio, TX (US)

(*) Notice: Subject to any disclaimer, the term of this patent is extended or adjusted under 35 U.S.C. 154(b) by 777 days.

(21) Appl. No.: 14/869,731

(22) Filed: Sep. 29, 2015

(65) Prior Publication Data

US 2016/0095754 A1   Apr. 7, 2016

Related U.S. Application Data

(60) Provisional application No. 62/096,669, filed on Dec. 24, 2014, provisional application No. 62/060,098, filed on Oct. 6, 2014.

(51) Int. Cl.
*A61F 13/00* (2006.01)
*A61L 15/18* (2006.01)
(Continued)

(52) U.S. Cl.
CPC ........ *A61L 15/18* (2013.01); *A61F 13/00068* (2013.01); *A61F 13/00987* (2013.01);
(Continued)

(58) Field of Classification Search
CPC .......... A61F 13/00; A61L 15/18; A61L 15/22; A61L 15/24; A61L 15/26; A51L 15/28; A61M 1/00
See application file for complete search history.

(56) References Cited

U.S. PATENT DOCUMENTS 1,355,846 A   10/1920   Rannells
2,547,758 A   4/1951   Kelling
(Continued)

FOREIGN PATENT DOCUMENTS

AU   550575 B2   3/1986
AU   745271 B2   3/2002
(Continued)

OTHER PUBLICATIONS

International Search Report for corresponding PCT/US2015/053031 dated Nov. 25, 2015.
(Continued)

*Primary Examiner* — Tatyana Zalukaeva
*Assistant Examiner* — Ilya Y Treyger

(57) ABSTRACT

Systems, methods, and apparatuses for forming a multi-function core for a dressing are described. The multi-function core includes a contact layer configured to be positioned adjacent to a tissue site, a wicking layer adjacent to the contact layer, an ion exchange layer adjacent to the wicking layer, an absorbing layer adjacent to the ion exchange layer, a blocking layer adjacent to the absorbing layer, and an odor-absorbing layer adjacent to the blocking layer. The contact layer, the wicking layer, the ion exchange layer, the absorbing layer, the blocking layer, and the odor-absorbing layer are coextensive and formed from a plurality of fibers disposed in a fibrous web. Methods of manufacturing the multi-function core are also described.

34 Claims, 6 Drawing Sheets

(51) Int. Cl.

| | |
|---|---|
| *A61L 15/22* | (2006.01) |
| *A61L 15/24* | (2006.01) |
| *A61L 15/26* | (2006.01) |
| *A61L 15/28* | (2006.01) |
| *A61M 1/00* | (2006.01) |
| *G05B 19/418* | (2006.01) |
| *A61L 15/44* | (2006.01) |
| *A61L 15/60* | (2006.01) |
| *A61F 13/02* | (2006.01) |
| *A61L 15/42* | (2006.01) |

(52) U.S. Cl.
CPC ...... *A61F 13/00991* (2013.01); *A61F 13/022* (2013.01); *A61F 13/0276* (2013.01); *A61L 15/22* (2013.01); *A61L 15/225* (2013.01); *A61L 15/24* (2013.01); *A61L 15/26* (2013.01); *A61L 15/28* (2013.01); *A61L 15/425* (2013.01); *A61L 15/44* (2013.01); *A61L 15/60* (2013.01); *A61M 1/0001* (2013.01); *A61M 1/0088* (2013.01); *G05B 19/41865* (2013.01); *A61F 2013/00314* (2013.01); *A61L 2300/104* (2013.01); *A61L 2300/106* (2013.01); *A61L 2300/404* (2013.01); *A61L 2420/00* (2013.01)

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,798,850 A | 7/1957 | Voigtman et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,287,153 A | 9/1981 | Towsend |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,538 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,818,598 A | 4/1989 | Wong |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,124,391 A | 9/2000 | Sun et al. |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,528,157 B1 | 3/2003 | Hussain et al. |
| 6,553,998 B2 | 4/2003 | Heaton et al. |
| 6,610,898 B1 | 8/2003 | Magnusson et al. |
| 6,814,079 B2 | 11/2004 | Heaton et al. |
| 7,846,141 B2 | 12/2010 | Weston |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,398,614 B2 | 3/2013 | Blott et al. |
| 8,449,509 B2 | 5/2013 | Weston |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,679,081 B2 | 3/2014 | Heagle et al. |
| 8,834,451 B2 | 9/2014 | Blott et al. |
| 8,926,592 B2 | 1/2015 | Blott et al. |
| 9,017,302 B2 | 4/2015 | Vitaris et al. |
| 9,198,801 B2 | 12/2015 | Weston |
| 9,211,365 B2 | 12/2015 | Weston |
| 9,289,542 B2 | 3/2016 | Blott et al. |
| 2002/0040210 A1 | 4/2002 | Luccio et al. |
| 2002/0077661 A1 | 6/2002 | Saadat |
| 2002/0115951 A1 | 8/2002 | Norstrem et al. |
| 2002/0120185 A1 | 8/2002 | Johnson |

(56) References Cited

U.S. PATENT DOCUMENTS

| | | | |
|---|---|---|---|
| 2002/0143286 A1 | 10/2002 | Tumey | |
| 2002/0168912 A1 | 11/2002 | Bond et al. | |
| 2002/0193030 A1 | 12/2002 | Yao et al. | |
| 2003/0138631 A1 | 7/2003 | Mitchell et al. | |
| 2005/0031850 A1 | 2/2005 | Mitchell et al. | |
| 2005/0124799 A1 | 6/2005 | Pesce et al. | |
| 2005/0130540 A1 | 6/2005 | Crane | |
| 2005/0147657 A1* | 7/2005 | Canada | A61K 31/4172 424/445 |
| 2005/0194141 A1 | 9/2005 | Sinclair et al. | |
| 2005/0247472 A1 | 11/2005 | Helfer et al. | |
| 2007/0044903 A1 | 3/2007 | Wisneski et al. | |
| 2007/0250024 A1 | 10/2007 | Mitchell et al. | |
| 2008/0011674 A1 | 1/2008 | Nakagaki et al. | |
| 2008/0202539 A1 | 8/2008 | Banks et al. | |
| 2009/0227969 A1 | 9/2009 | Jaeb et al. | |
| 2010/0003517 A1 | 1/2010 | Hansson | |
| 2010/0298793 A1 | 11/2010 | Blott et al. | |
| 2010/0323945 A1 | 12/2010 | Simonsen | |
| 2011/0082105 A1 | 4/2011 | Fevola et al. | |
| 2012/0055643 A1 | 3/2012 | Neal et al. | |
| 2013/0096524 A1 | 4/2013 | Riesinger | |
| 2013/0150764 A1 | 6/2013 | Patel et al. | |
| 2013/0218110 A1 | 8/2013 | Olson | |
| 2013/0317406 A1 | 11/2013 | Locke et al. | |
| 2014/0026910 A1 | 1/2014 | Bundren et al. | |
| 2014/0138305 A1 | 5/2014 | Crandall et al. | |
| 2014/0163491 A1 | 6/2014 | Schuessler et al. | |
| 2014/0200532 A1 | 7/2014 | Robinson et al. | |
| 2014/0249495 A1 | 9/2014 | Mumby et al. | |
| 2015/0025436 A1 | 1/2015 | Tang et al. | |
| 2015/0080788 A1 | 3/2015 | Blott et al. | |
| 2016/0222548 A1 | 8/2016 | Agboh | |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| JP | 2014-121194 A | 6/2014 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |
| WO | 2005051461 A1 | 6/2005 |
| WO | 2009097534 A1 | 8/2009 |
| WO | 2009111657 A2 | 9/2009 |
| WO | 2009157877 A1 | 12/2009 |
| WO | 2013007973 A2 | 1/2013 |

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery.

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 198, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & Apr. 29, 1997.

PCT Written Opinion, PCT International Application PCT/GB96/02802; dated Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

(56) References Cited

OTHER PUBLICATIONS

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96.

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164.

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R, 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians; Jul. 2007.

Extended European Search Report for Corresponding Application No. 181938945, dated Dec. 21, 2018.

International Search Report and Written Opinion corresponding to PCT Application No. PCT/US2015/053018 dated Nov. 17, 2015.

James Economy et al: "Polymeric Ion-Exchange Fibers", Industrial & Engineering Chemistry Research, vol. 41, No. 25, Dec. 1, 2002, pp. 6436-6442.

Extended European Search Report for Corresponding Application No. 181935628, dated Jan. 4, 2019.

Japanese Notice of Rejection corresponding to Application No. 2017-518206, dated Jul. 16, 2019.

\* cited by examiner

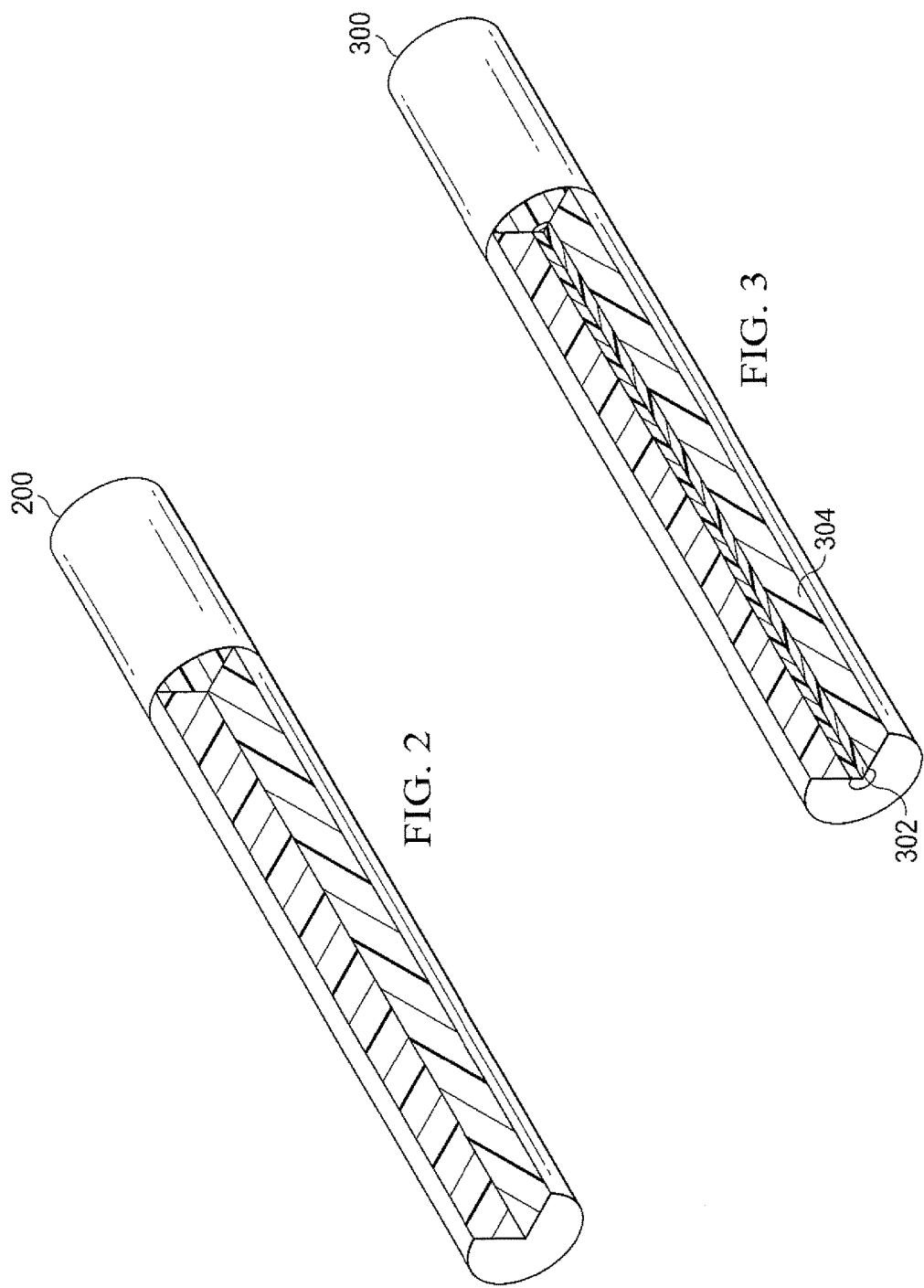

MULTI-FUNCTION DRESSING STRUCTURE FOR NEGATIVE-PRESSURE THERAPY

This application claims priority to and the benefit of U.S. Provisional Patent Application No. 62/060,098, filed Oct. 6, 2014, entitled "Multi-Function Dressing Structure for Negative Pressure Therapy," to Robinson et al., and U.S. Provisional Patent Application No. 62/096,669, filed Dec. 24, 2014, entitled "Ion Exchange Absorbent Systems, Apparatuses, and Methods, to Locke et al., both of which are hereby incorporated by reference.

TECHNICAL FIELD

The invention set forth in the appended claims relates generally to tissue treatment systems and more particularly, but without limitation, to a multi-function dressing structure for negative-pressure therapy.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," and "vacuum-assisted closure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

While the clinical benefits of negative-pressure therapy are widely known, the cost and complexity of negative-pressure therapy can be a limiting factor in its application, and the development and operation of negative-pressure systems, components, and processes continues to present significant challenges to manufacturers, healthcare providers, and patients.

BRIEF SUMMARY

New and useful systems, apparatuses, and methods for a multi-function core in a negative-pressure therapy environment are set forth in the appended claims. Illustrative embodiments are also provided to enable a person skilled in the art to make and use the claimed subject matter. For example, a multi-function core is described herein. The multi-function core may include a contact layer configured to be positioned adjacent to a tissue site, a wicking layer adjacent to the contact layer, an ion exchange layer adjacent to the wicking layer, an absorbing layer adjacent to the ion exchange layer, a blocking layer adjacent to the absorbing layer, and an odor-absorbing layer adjacent to the blocking layer. The contact layer, the wicking layer, the ion exchange layer, the absorbing layer, the blocking layer, and the odor-absorbing layer may be formed from a plurality of fibers disposed in a fibrous web.

In another example embodiment, a system for providing negative-pressure therapy to a tissue site is described. The system may include a manifold configured to be positioned adjacent to the tissue site and a cover configured to be placed over the manifold and sealed to tissue surrounding the tissue site to form a sealed space. A negative-pressure source may be configured to be fluidly coupled to the sealed space, and a multi-function core may be configured to be positioned between the manifold and the cover. The multi-function core may include a wound interface layer configured to be positioned over the manifold, a fluid dispersion layer positioned over the wound interface layer, an ion removal layer positioned over the fluid dispersion layer, a liquid retention layer positioned over the ion removal layer, a liquid obstruction layer positioned over the liquid retention layer, and an odor removal layer positioned over the liquid obstruction layer.

In still other embodiments, a method for providing negative-pressure therapy to a tissue site is described. A tissue interface may be positioned adjacent to the tissue site, and a sealing member may be placed over the tissue interface and sealed to tissue surrounding the tissue site to form a sealed space. A negative-pressure source may be fluidly coupled to the sealed space. A fluid management apparatus may be positioned between the tissue interface and the sealing member. The fluid management apparatus may include a contact layer configured to be positioned adjacent to the tissue interface, a fluid dispersion layer coupled to the contact layer, an ion exchange layer coupled to the fluid dispersion layer, a liquid retention layer coupled to the ion exchange layer, a liquid blocking layer coupled to the liquid retention layer, and an odor removal layer coupled to the liquid blocking layer. The negative-pressure source may be operated to draw fluid from the sealed space through the fluid management apparatus and generate a negative pressure in the sealed space.

In yet another embodiment, a method of manufacturing a multi-function core for a negative-pressure dressing is described. One or more plurality of fibers may be formed in respective workstations of a plurality of workstations. The plurality of fibers may be disposed into a fibrous web in the respective workstations of the plurality of workstations. The layers may be coupled to each other to form a multi-function sheet. The multi-function sheet having the layers may be subdivided into multi-function cores.

Objectives, advantages, and a preferred mode of making and using the claimed subject matter may be understood best by reference to the accompanying drawings in conjunction with the following detailed description of illustrative embodiments.

BRIEF DESCRIPTION OF THE DRAWINGS

FIG. 2 is a perspective view, with a portion shown in cross-section, of an example embodiment of a fiber of the multi-function core of FIG. 1;

FIG. 3 is a perspective view, with a portion shown in cross-section, of an example embodiment of a dual-layer fiber of the multi-function core of FIG. 1;

DESCRIPTION OF EXAMPLE EMBODIMENTS

The following description of example embodiments provides information that enables a person skilled in the art to make and use the subject matter set forth in the appended claims, but may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

Figure 1:
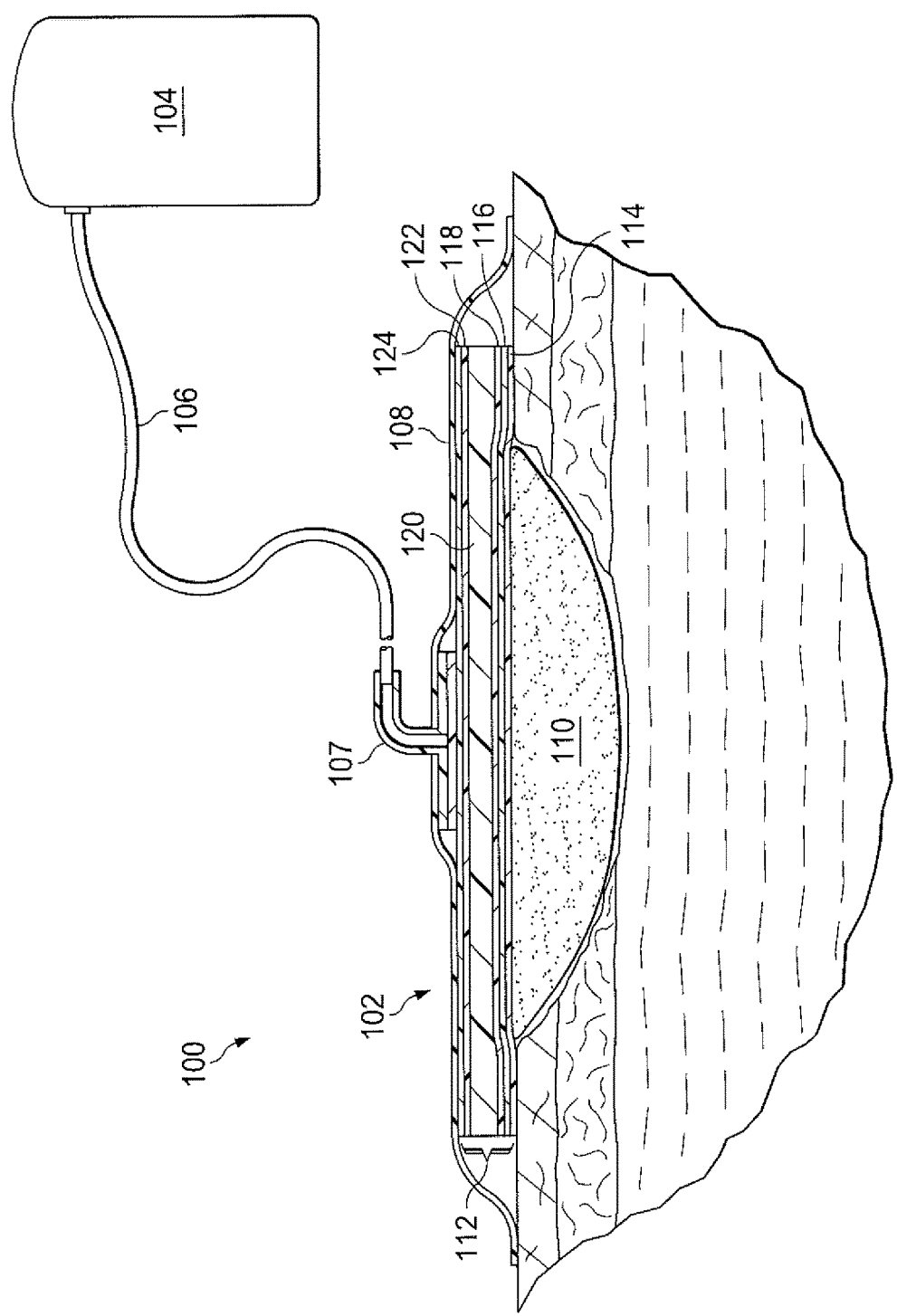
FIG. 1 is sectional view of an example embodiment of a negative-pressure therapy system that can provide negative-pressure therapy in accordance with this specification.

FIG. 1 is a sectional view with a portion shown in elevation of an example embodiment of a negative-pressure therapy system 100 that can provide negative-pressure therapy in accordance with this specification. The negative-pressure therapy system 100 may include a dressing 102 and a negative-pressure source 104. For example, a dressing 102 may be fluidly coupled to a negative-pressure source 104, as illustrated in FIG. 1. In some embodiments, the negative-pressure source 104 may be fluidly coupled to the dressing 102 by a tube 106 and a connector 107. A dressing generally includes a cover and a tissue interface. The dressing 102, for example, includes a cover 108, and a tissue interface 110. The dressing 102 may also include a fluid management core, such as a core 112.

In general, components of the negative-pressure therapy system 100 may be coupled directly or indirectly. For example, the negative-pressure source 104 may be directly coupled to the connector 107 and indirectly coupled to the dressing 102 through the connector 107. Components may be fluidly coupled to each other to provide a path for transferring fluids (i.e., liquid and/or gas) between the components.

In some embodiments, for example, components may be fluidly coupled through a tube. A "tube," as used herein, broadly refers to a tube, pipe, hose, conduit, or other structure with one or more lumina adapted to convey a fluid between two ends. Typically, a tube is an elongated, cylindrical structure with some flexibility, but the geometry and rigidity may vary. In some embodiments, components may additionally or alternatively be coupled by virtue of physical proximity, being integral to a single structure, or being formed from the same piece of material. Coupling may also include mechanical, thermal, electrical, or chemical coupling (such as a chemical bond) in some contexts.

In operation, the tissue interface 110 may be placed within, over, on, or otherwise proximate to a tissue site. The cover 108 may be placed over the tissue interface 110 and sealed to tissue near the tissue site. For example, the cover 108 may be sealed to undamaged epidermis peripheral to a tissue site. Thus, the dressing 102 can provide a sealed therapeutic environment proximate to a tissue site, substantially isolated from the external environment, and the negative-pressure source 104 can reduce the pressure in the sealed therapeutic environment. Negative pressure applied across the tissue site through the tissue interface 110 in the sealed therapeutic environment can induce macrostrain and microstrain in the tissue site, as well as remove exudates and other fluids from the tissue site, which can be collected in the dressing core 112 and disposed of properly.

The fluid mechanics of using a negative-pressure source to reduce pressure in another component or location, such as within a sealed therapeutic environment, can be mathematically complex. However, the basic principles of fluid mechanics applicable to negative-pressure therapy are generally well-known to those skilled in the art, and the process of reducing pressure may be described illustratively herein as "delivering," "distributing," or "generating" negative pressure, for example.

In general, exudates and other fluids flow toward lower pressure along a fluid path. Thus, the term "downstream" typically implies a position in a fluid path relatively closer to a negative-pressure source, and conversely, the term "upstream" implies a position relatively further away from a negative-pressure source. Similarly, it may be convenient to describe certain features in terms of fluid "inlet" or "outlet" in such a frame of reference. This orientation is generally presumed for purposes of describing various features and components of negative-pressure therapy systems herein. However, the fluid path may also be reversed in some applications (such as by substituting a positive-pressure source for a negative-pressure source) and this descriptive convention should not be construed as a limiting convention.

The term "tissue site" in this context broadly refers to a wound or defect located on or within tissue, including but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue. For example, negative pressure may be used in certain tissue areas to grow additional tissue that may be harvested and transplanted to another tissue location.

"Negative pressure" generally refers to a pressure less than a local ambient pressure, such as the ambient pressure in a local environment external to a sealed therapeutic environment provided by the dressing 102. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. Similarly, references to increases in negative pressure typically refer to a decrease in absolute pressure, while decreases in negative pressure typically refer to an increase in absolute pressure.

A negative-pressure source, such as the negative-pressure source 104, may be a reservoir of air at a negative pressure, or may be a manual or electrically-powered device that can reduce the pressure in a sealed volume, such as a vacuum pump, a suction pump, a wall suction port available at many healthcare facilities, or a micro-pump, for example. A negative-pressure source may be housed within or used in conjunction with other components, such as sensors, processing units, alarm indicators, memory, databases, software, display devices, or user interfaces that further facilitate negative-pressure therapy. While the amount and nature of negative pressure applied to a tissue site may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −75 mm Hg (−9.9 kPa) and −300 mm Hg (−39.9 kPa).

The tissue interface 110 can be generally adapted to contact a tissue site. The tissue interface 110 may be partially or fully in contact with the tissue site. If the tissue site is a wound, for example, the tissue interface 110 may partially or completely fill the wound, or may be placed over the wound. The tissue interface 110 may take many forms, and may have many sizes, shapes, or thicknesses depending on a variety of factors, such as the type of treatment being implemented or the nature and size of a tissue site. For example, the size and shape of the tissue interface 110 may be adapted to the contours of deep and irregular shaped tissue sites.

In some embodiments, the tissue interface 110 may be a manifold. A "manifold" in this context generally includes any substance or structure providing a plurality of pathways adapted to collect or distribute fluid across a tissue site under negative pressure. For example, a manifold may be adapted to receive negative pressure from a source and distribute the negative pressure through multiple apertures across a tissue site, which may have the effect of collecting fluid from across a tissue site and drawing the fluid toward the source. In some embodiments, the fluid path may be reversed or a secondary fluid path may be provided to facilitate delivering fluid across a tissue site.

In some illustrative embodiments, the pathways of a manifold may be channels interconnected to improve distribution or collection of fluids across a tissue site. For example, cellular foam, open-cell foam, reticulated foam, porous tissue collections, and other porous material such as gauze or felted mat generally include pores, edges, and/or walls adapted to form interconnected fluid pathways. Liquids, gels, and other foams may also include or be cured to include apertures and flow channels. In some illustrative embodiments, a manifold may be a porous foam material having interconnected cells or pores adapted to uniformly (or quasi-uniformly) distribute negative pressure to a tissue site. The foam material may be either hydrophobic or hydrophilic. In one non-limiting example, a manifold may be an open-cell, reticulated polyurethane foam such as GranuFoam® dressing available from Kinetic Concepts, Inc. of San Antonio, Tex.

In an example in which the tissue interface 110 may be made from a hydrophilic material, the tissue interface 110 may also wick fluid away from a tissue site, while continuing to distribute negative pressure to the tissue site. The wicking properties of the tissue interface 110 may draw fluid away from a tissue site by capillary flow or other wicking mechanisms. An example of a hydrophilic foam is a polyvinyl alcohol, open-cell foam such as V.A.C. WhiteFoam® dressing available from Kinetic Concepts, Inc. of San Antonio, Tex. Other hydrophilic foams may include those made from polyether. Other foams that may exhibit hydrophilic characteristics include hydrophobic foams that have been treated or coated to provide hydrophilicity.

The tissue interface 110 may further promote granulation at a tissue site when pressure within the sealed therapeutic environment is reduced. For example, any or all of the surfaces of the tissue interface 110 may have an uneven, coarse, or jagged profile that can induce microstrains and stresses at a tissue site if negative pressure is applied through the tissue interface 110.

In some embodiments, the tissue interface 110 may be constructed from bioresorbable materials. Suitable bioresorbable materials may include, without limitation, a polymeric blend of polylactic acid (PLA) and polyglycolic acid (PGA). The polymeric blend may also include without limitation polycarbonates, polyfumarates, and capralactones. The tissue interface 110 may further serve as a scaffold for new cell-growth, or a scaffold material may be used in conjunction with the tissue interface 110 to promote cell-growth. A scaffold is generally a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

In some embodiments, a sealing member, such as the cover 108, may provide a bacterial barrier and protection from physical trauma. The cover 108 may also be constructed from a material that can reduce evaporative losses and provide a fluid seal between two components or two environments, such as between a therapeutic environment and a local external environment. The cover 108 may be, for example, an elastomeric film or membrane that can provide a seal adequate to maintain a negative pressure at a tissue site for a given negative-pressure source. In some example embodiments, the cover 108 may be a polymer drape, such as a polyurethane film, that is permeable to water vapor but impermeable to liquid. Such drapes typically have a thickness in the range of 25-50 microns. For permeable materials, the permeability generally should be low enough that a desired negative pressure may be maintained.

An attachment device may be used to attach the cover 108 to an attachment surface, such as undamaged epidermis, a gasket, or another cover. The attachment device may take many forms. For example, an attachment device may be a medically-acceptable, pressure-sensitive adhesive that extends about a periphery, a portion, or an entire sealing member. In some embodiments, for example, some or all of the cover 108 may be coated with an acrylic adhesive having a coating weight between 25-65 g.s.m. Thicker adhesives, or combinations of adhesives, may be applied in some embodiments to improve the seal and reduce leaks. Other example embodiments of an attachment device may include a double-sided tape, paste, hydrocolloid, hydrogel, silicone gel, or organogel.

Tissue sites may produce fluids that can be removed by negative pressure. Fluids removed from a tissue site can be collected for subsequent disposal or analysis. For example, a canister may be fluidly coupled to a dressing to collect fluids from a wound. Such canisters are readily available and can be relatively inexpensive. However, canisters can also be cumbersome and limit patient mobility. Some dressings can absorb fluids, which can enhance patient mobility, but manufacturing a dressing with adequate fluid capacity can be complex and expensive.

A fluid management core such as the core 112 can reduce the cost and complexity of manufacturing a dressing with fluid storage capacity. For example, in some embodiments, a multi-function core may include six or more layers that provide skin contact, fluid wicking, ion exchange, liquid absorbing, liquid blocking, and odor absorbing functions in a unitary apparatus. A dressing may be manufactured by a process that produces each layer as a part and assembles the multi-function core in a process that reduces manufacturing time and costs.

As shown in FIG. 1, the core 112 may be a multi-function core or fluid management apparatus having multiple layers that can be configured to accomplish different functions. In some embodiments, the core 112 may include six layers. For example, the core 112 may have a wound interface layer or contact layer 114, a fluid dispersion layer or wicking layer 116, an ion removal layer or ion exchange layer 118, a liquid retention layer or absorbing layer 120, a liquid obstruction layer or blocking layer 122, and an odor removal layer or odor absorbing layer 124. Each layer may be formed from a plurality of fibers disposed in a fibrous web. In some embodiments, a fibrous web may include a plurality of fibers positioned so that individual fibers overlap and are coupled to one another to form open spaces between adjacent fibers. The fibrous web may be a woven or non-woven. In some embodiments, the plurality of fibers may be single-layer fibers. In some embodiments, the plurality of fibers may be dual-layer fibers. In some embodiments, the fibers of a particular layer may be both single-layer and dual-layer fibers. The core 112 may have a high moisture vapor transfer rate (MVTR) and gas permeability across the structure such that dry negative pressure, that is, air having little or no moisture content, may be manifolded across the entire area of the core 112. In some embodiments, the core 112 may have an MVTR between about 250 g/m$^2$/day and about 2000 g/m$^2$/day when measured at 37° C. and 50%/relative humidity using the upright cup method. In some embodiments, the core 112 may have a gas permeability of oxygen of about 50 cm$^3$/m$^2$/day/MPa.

FIG. 2 is a partial sectional view of a single-layer fiber 200, illustrating additional details that may be associated with some example embodiments. The single-layer fiber 200 may have a diameter in the range of about 1 micron to about 50 microns. The single-layer fiber 200 may be a fiber having a substantially homogenous composition. For example, the single-layer fiber 200 may be formed from a single material, such as polyurethane, polyester, acrylic, fluorocarbon, or silicone. In some embodiments, the single-layer fiber 200 may be associated with additional materials, such as activated carbon particles or superabsorbent polymer particles or fibers. For example, the single-layer fiber 200 may be formed from silicone and have activated carbon particles disposed within or on the silicone. The single-layer fiber 200 may be formed by melt-blown fiber formation, melt-spinning fiber formation, wet-spinning fiber formation, or solution-based electro spinning.

Melt blown fiber formation may involve extruding melted polymers through a spin net or die to produce fibers. Hot air may be blown over the fibers to stretch and cool the fibers as the fibers pass out of the spin net or die. Melt spinning may involve melting a polymer and squeezing the melted polymer through a spinneret to form a fiber. For example, silicone may be mixed with glycerol and deionized water to form a solution. The solution may be fed into an extruder spinning system to form fibers. Wet spinning may involve dissolving the polymer to form a coagulating bath having a low pH. Liquid in the coagulating bath may be evaporated to form a fine fiber. For example, silicone can be processed by a cylinder spinning system to spin a thread that may be coagulated in a bath, air dried, and wound on a bobbin. Electrospinning may subject a polymer solution to an electric field to induce the accumulation of a charge on the surface of a pendant drop. The charge accumulation generates a force that directly opposes the force produced by the surface tension of the drop that, above a critical value of electric field strength, can cause a charged jet to eject to form fine filaments. The filaments may then be cut into standardized lengths to form staple fibers. In some embodiments, the staple fibers may have a length between about 4 mm and about 6 mm. The staple fibers may be twisted together and carded to form the single-layer fiber 200.

FIG. 3 is a partial sectional view of a dual-layer fiber 300, illustrating additional details that may be associated with some example embodiments. The dual-layer fiber 300 may have an inner core 302 and an outer sheathing 304. In some embodiments, the inner core 302 may be a fiber having a substantially homogenous composition. For example, the inner core 302 may be formed from a single material, such as polyurethane, polyester, acrylic, fluorocarbon, or silicone. In some embodiments, the inner core 302 may be associated with additional materials, such as activated carbon particles or antimicrobials. For example, the inner core 302 may be formed from silicone and have activated carbon particles disposed within or on the silicone. The inner core 302 may be formed by melt-blown fiber formation, melt-spinning fiber formation, wet-spinning fiber formation, or solution-based electro spinning. In some embodiments, the inner core 302 may have a diameter in the range of about 0.75 microns to about 75 microns. The outer sheathing 304 may be a coating of a material that is different than the material of the inner core 302. In some embodiments, the outer sheathing 304 may be formed from a silicone gel or hydrophilic polyurethane. In some embodiments, the outer sheathing 304 may have a thickness between about 0 microns and about 12.5 microns. In some embodiments, the dual-layer fiber 300 may have an overall diameter between about 0.75 microns and about 100 microns.

Figure 4:
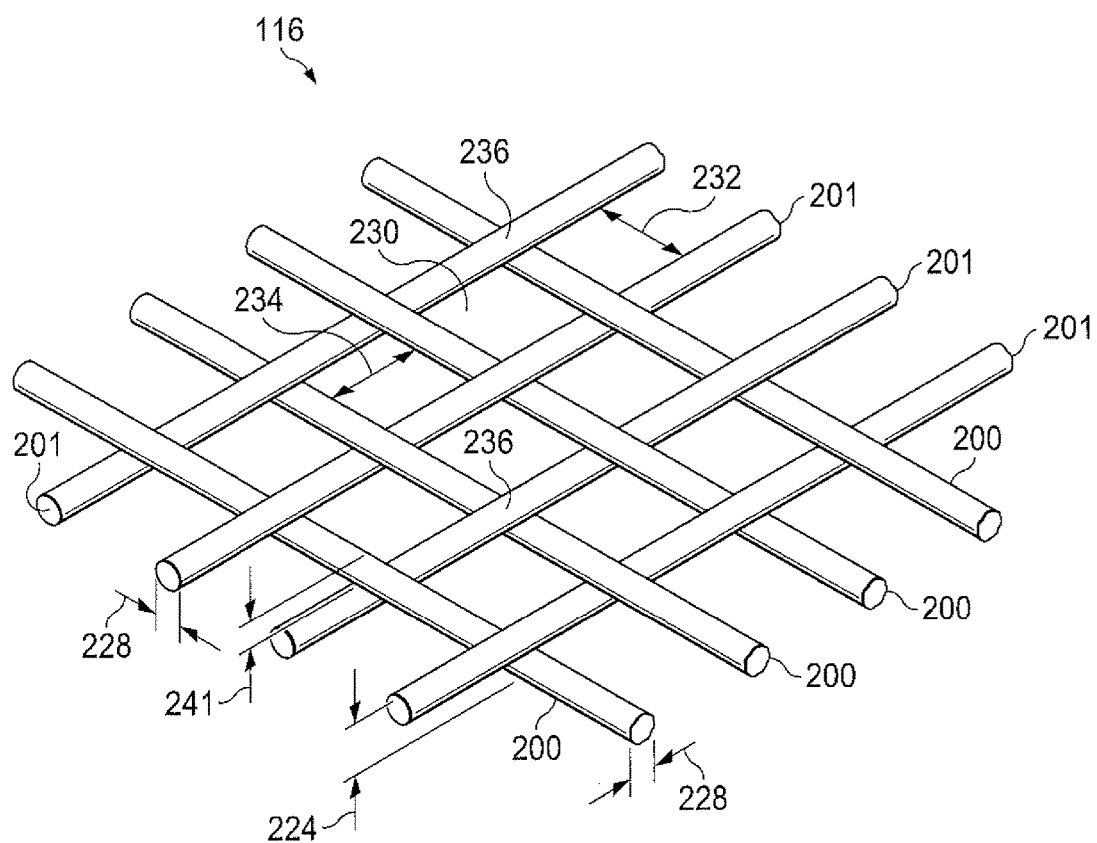
FIG. 4 is a perspective view illustrating additional details of a woven layer of the multi-function core of FIG. 1.

FIG. 4 is a perspective view of a portion of a layer that may be associated with some embodiments of the core 112. For example, the layer may be the wicking layer 116 having a woven structure as illustrated in FIG. 4. A woven generally refers to a fabric-like material formed by weaving, knitting, lace-making, felting, braiding, or plaiting fibers so that the fibers are interlaced. Although the wicking layer 116 is illustrated in FIG. 4, any or all of the contact layer 114, the ion exchange layer 118, and the absorbing layer 120 may also be formed as a woven analogous to the wicking layer 116. In some embodiments, the fibers of a woven layer may be single-layer fibers 200. In some embodiments, the fibers of a woven layer may be dual-layer fibers 300. In some embodiments, for example, the wicking layer 116 may be formed by weaving the single-layer fibers 200 to form a regular pattern of openings or mesh apertures 230. As illustrated in FIG. 4, the wicking layer 116 may comprise a first plurality of single-layer fibers 200 aligned substantially parallel to each other and a second plurality of single-layer fibers 201 also aligned substantially parallel to each other, wherein the fibers 200 are disposed adjacent to the fibers 201 at an angle. In some embodiments, the fibers 200 may be perpendicular to the fibers 201. The fibers 200 and the fibers 201 may overlap each other to form a weave or mesh having the plurality of apertures 230. The fibers 200 may intersect with the fibers 201 to form a plurality of intersections 236. An intersection 236 may be formed by overlapping fibers. In some embodiments, the fibers 200 and the fibers 201 may be woven together to form a network or a mesh.

The first fibers 200 and the second fibers may be separated from adjacent fibers 200 and fibers 201, respectively, by a distance 232 and 234, respectively, which may be between about 0.5 mm and about 5 mm. In other embodiments, the distance 232 and 234 may be between about 1.0 mm and about 2.5 mm. In some embodiments, the distance 232 and the distance 234 may be the substantially equal. In other embodiments, the distance 232 and the distance 234 may be different.

In some embodiments, the mesh apertures 230 may have an average effective diameter of about 2 mm. An effective diameter of a non-circular area may be a diameter of a circular area having the same surface area as the non-circular area. For example, the surface area of a mesh aperture 230 where the distance 232 is 0.5 mm and the distance 234 is 0.5 mm may be 0.25 mm². The diameter of a circular area having a 0.25 mm² surface area is about 0.56 mm; consequently, the effective diameter of the exemplary mesh aperture 230 is about 0.56 mm. Similarly, if the distance 232 is about 4 mm and the distance 234 is about 4 mm, the effective diameter of the mesh aperture 230 may be about 4.51 mm. In some embodiments, each mesh aperture 230 may have an area formed by the effective diameter of the mesh aperture 230. In some embodiments, each mesh aperture 230 may be uniform in area. In other embodiments, each mesh aperture 230 may not be uniform in area. If the mesh apertures 230 are not uniform in area, the average of the areas of the mesh apertures 230 may be between about 0.2 mm² and about 20 mm². Each of the contact layer 114, the wicking layer 116, the ion exchange layer 118, the absorbing layer 120, the blocking layer 122, and the odor absorbing layer 124 may have mesh apertures 230 between about 0.2 mm² and about 20 mm².

In some embodiments, each of the single-layer fibers 200, 201 of the wicking layer 116 may have a diameter 228. In other embodiments, the diameters of the single-layer fibers 200, 201 may be different. The intersections 236 may have a prominence 241. In some embodiments, the prominence 241 at the intersections 236 may be equal to the diameter 228 of the single-layer fibers 200, 201. In some embodiments, the prominence 241 may be reduced by compressing the wicking layer 116 following formation of the wicking layer 116. The prominences 241 may also be reduced by passing the wicking layer 116 through a calender, which may apply pressure to the wicking layer 116 to smooth out the wicking layer 116. Each of the contact layer 114, the wicking layer 116, the ion exchange layer 118, the absorbing layer 120, the blocking layer 122, and the odor absorbing layer 124 may have prominences 241. The wicking layer 116 may have a thickness 224. In some embodiments, the thickness 224 may be the combined thickness of the diameters 228 of the single-layer fibers 200, 201.

Figure 5:
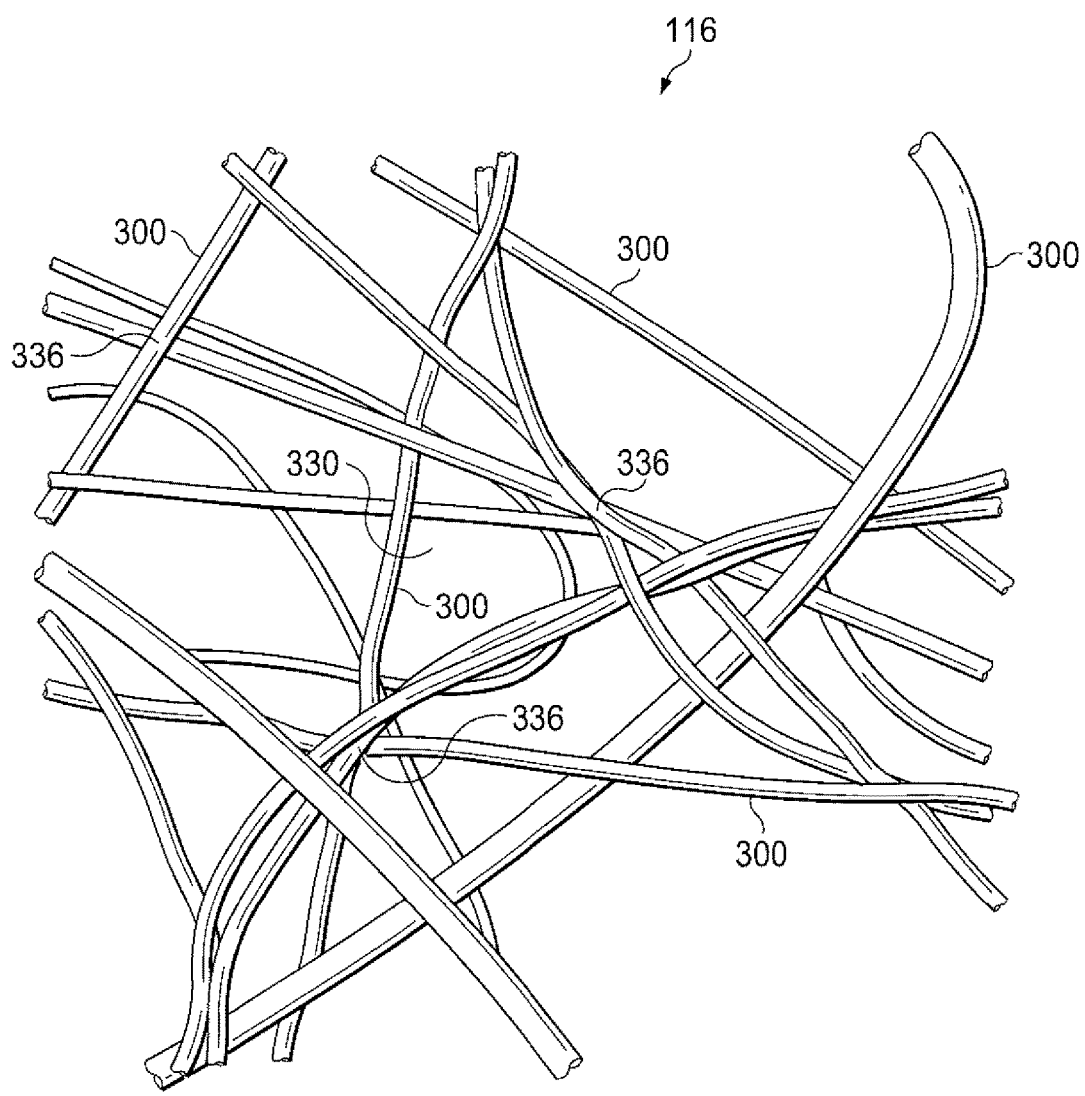
FIG. 5 is a plan view illustrating additional details of a non-woven layer of the multi-function core of FIG. 1.

FIG. 5 is a schematic view of a portion of a non-woven layer, such as the wicking layer 116, illustrating additional details that may be associated with other example embodiments of the negative-pressure therapy system 100. A non-woven may be a layer of fabric-like material made from long fibers that may be bonded together by chemical, mechanical, heat, or solvent treatment. Non-wovens may be melt blown, air laid, thermo bonded, and spun bonded, for example. Each of the contact layer 114, the ion exchange layer 118, the absorbing layer 120, the blocking layer 122, and the odor-absorbing layer 124 may be formed as a non-woven as described with respect to the wicking layer 116 herein. The non-woven wicking layer 116 may operate similarly or analogously to the woven wicking layer 116. Similar elements may have similar reference numbers that are indexed to 300. In some embodiments, a plurality of dual-layer fibers 300 may be formed into the non-woven wicking layer 116. For example, the dual-layer fibers 300 may be dispersed on a conveyor belt, and spread in a uniform web by a wetlaid, an airlaid, or a carding/crosslapping process. The dual-layer fibers 300 may be bonded thermally or by using a resin to form the mesh of the wicking layer 116. For example, the dual-layer fibers 300 may overlap and form intersections 336 where the dual-layer fibers 300 overlap with other dual-layer fibers 300. The overlapping dual-layer fibers 300 of the wicking layer 116 may also form openings, such as mesh apertures 330. As shown in FIG. 5, the mesh apertures 330 may not be uniform in shape. The mesh apertures 330 of the wicking layer 116 may have an average effective diameter between about 1 mm and about 5 mm. If the mesh apertures 330 are not uniform in size the average of the effective diameters of each of the mesh apertures 330 may be between about 1 mm and about 5 mm.

In some embodiments, the wicking layer 116 may also be formed in a spunlaid process. Spunlaid non-wovens may be made in a continuous process. The dual-layer fibers 300 may be dispersed into a web by physical deflectors or with air streams as the dual-layer fibers 300 are produced without further cutting the dual-layer fibers 300.

Generally, a thickness of the non-woven wicking layer 116, the dual-layer fibers 300, a diameter of the dual-layer fibers 300, the mesh apertures 330, and the intersections 336 may be similar to and operate as described above with respect to the woven wicking layer 116, the thickness 224 of the wicking layer 116, the single-layer fibers 200, 201, the diameter 228, the mesh apertures 230, and the intersections 236, respectively.

Figure 6:
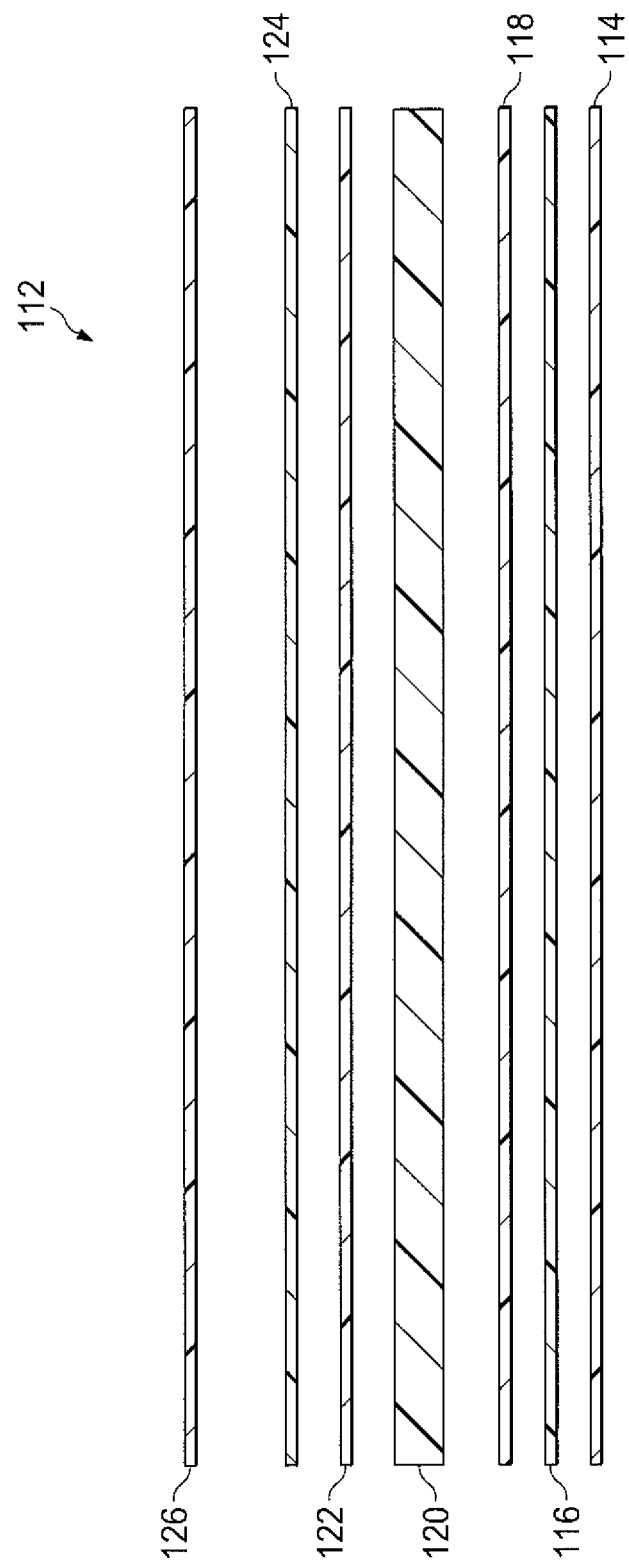
FIG. 6 is a schematic sectional exploded view illustrating additional details that may be associated with an example embodiment of a multi-function core of the negative-pressure therapy system of FIG. 1.

FIG. 6 is a schematic sectional exploded view illustrating additional details that may be associated with an example embodiment of the multi-function core 112. In some embodiments, the contact layer 114, the wicking layer 116, the ion exchange layer 118, the absorbent layer 120, the blocking layer 122, the odor-absorbing layer 124, and the rigid layer 126 may be coextensive with one another. In other embodiments, one or more of the contact layer 114, the wicking layer 116, the ion exchange layer 118, the absorbent layer 120, the blocking layer 122, the odor-absorbing layer 124, and the rigid layer 126 may be coextensive with one another. In still other embodiments, the contact layer 114, the wicking layer 116, the ion exchange layer 118, the absorbent layer 120, the blocking layer 122, the odor-absorbing layer 124, and the rigid layer 126 may not be coextensive with one another. In some embodiments, one or more of the contact layer 114, the wicking layer 116, the ion exchange layer 118, the absorbent layer 120, the blocking layer 122, the odor-absorbing layer 124, and the rigid layer 126 may draw negative-pressure through the respective layer. In some embodiments, one or more of the contact layer 114, the wicking layer 116, the ion exchange layer 118, the absorbent layer 120, the odor-absorbing layer 124, and the rigid layer 126 may be liquid permeable.

The contact layer 114 may be formed from a plurality of dual-layer fibers 300 formed into a woven or non-woven layer of material. In some embodiments, the contact layer 114 may have a thickness between about 0.5 millimeters (mm) and about 2 mm. In some embodiments, the dual-layer fibers 300 may have the inner core 302 formed from a hydrophobic polyurethane and the outer sheathing 304 formed from a silicone gel. In other embodiments, the inner core 302 may be a hydrophobic polyurethane core and the outer sheathing 304 may be a hydrophilic polyurethane. In some embodiments the hydrophilic polyurethane of the outer sheathing 304 may be a gel. In some embodiments, an antimicrobial, such as silver, may be dispersed in the outer sheathing 304 of the dual-layer fibers 300 of the contact layer 114. In some embodiments, an antimicrobial, such as iodine, may be dispersed in the inner core 302 of the dual-layer fibers 300 of the contact layer 114. In some embodiments, if the antimicrobial is disposed in the inner core 302 rather than the outer core 304, the antimicrobial may have a time-release property. In still other embodiments, the outer sheathing 304 may be formed from collagen. In some embodiments, the contact layer 114 may seal to epidermis surrounding a tissue site. In some embodiments, the contact layer 114 may be tacky to assist in forming a seal. For example, the contact layer 114 may have a tackiness or peel adhesion of about 0.2 N/cm on stainless steel substrate at 23° C. at 50% relative humidity based on the American Society for Testing and Materials ("ASTM") standard ASTM D3330. In some embodiments, the dual-layer fibers 300 may have a tensile strength of about 40 Newtons (N) per 5 cm length in the direction of the applied force with a tolerance of about +/−15%, and the contact layer 114 may permit fluid flow at about 0.83 cubic centimeters/ hour.

In some embodiments, the wicking layer 116 may be formed from a plurality of single-layer fibers 200 formed into a woven or a non-woven. In some embodiments, the wicking layer 116 may have a thickness between about 1 mm and about 4 mm. In some embodiments, the single-layer fibers 200 may be formed from a hydrophilic polymer such as polyurethane, polyester, or acrylic. In other embodiments, the wicking layer 116 may be formed from dual-layer fibers 300. If the wicking layer 116 is formed from dual-layer fibers 300, the inner core 302 may be formed from hydrophobic polyurethane, and the outer sheathing 304 may be formed from hydrophilic polyurethane. The hydrophobic polyurethane of the inner core 302 may provide more strength than the single-layer fiber 200 formed from the hydrophilic polyurethane alone. Generally, polyurethane may have a strength inversely proportional to its volumetric water content. By using a hydrophobic polyurethane to form the inner core 302, the inner core 302 of the dual-layer fiber 300 of the wicking layer 116 may resist water absorption, thereby increasing the strength of the dual-layer fiber 300. For example, the wicking layer 116 formed as a non-woven having the dual-layer fibers 300 may have a tensile strength of about 40 Newtons (N) per 5 cm length in the direction of the applied force with a tolerance of about +/−15%. In some embodiments, the wicking layer 116 may encourage fluid to spread at an angle to the direction of fluid flow. For example, if a negative-pressure source is drawing fluid through the wicking layer 116 parallel to the thickness of the wicking layer 116, the wicking layer 116 may encourage fluid to spread perpendicular to the thickness of the wicking layer 116. In some embodiments, the wicking layer 116 may permit fluid flow at about 0.83 cubic centimeters/hour or greater.

In some embodiments, the ion exchange layer 118 may be formed from a plurality of dual-layer fibers 300. In some embodiments, the ion exchange layer 118 may have a thickness in the range of 0.5 mm and about 2 mm, a flow rate of about 0.83 cubic centimeters/hour, and the dual-layer fibers 300 may have a tensile strength of about 40 Newtons (N) per 5 cm length in the direction of the applied force with a tolerance of about +/−15%.

The dual-layer fibers 300 of the ion exchange layer 118 may have an inner core 302 formed from a hydrophobic polymer, such as a hydrophobic polyurethane and an outer sheathing 304 formed from a hydrophilic polymer, such as a hydrophilic polyurethane. Ion exchange media (IEM) may be disposed in the outer sheathing 304. Generally, IEM may exchange both hydrogen and hydroxyl ions for cationic and anionic salt ions found in wound fluids, such as sodium, chloride, and calcium. In other embodiments, the ion exchange layer 118 may be formed from a single-layer fiber 200 formed from a hydrophilic polymer having activated carbon particles or fibers for ion exchange functionality.

IEM may be adapted to provide an exchange of ions between two electrolytes, or between an electrolyte solution and a complex. An electrolyte may be a compound that ionizes when dissolved in a suitable ionizing solvent, such as water. An electrolyte solution may contain a dissolved salt, such as NaCl. A complex may be an atom or ion having a surrounding array of bound molecules or anions known as ligands or complexing agents. IEM replaces cations and anions in an electrolyte or an electrolyte solution as the electrolyte or electrolyte solution interacts with the IEM. Cations are ions having a net positive charge, for example, Na+. Cations may be replaced in the electrolyte or electrolyte solution with hydrogen (H+) ions of the IEM. Anions are ions having a net negative charge, for example, Cl−. Anions may be replaced in the electrolyte or electrolyte solution with hydroxyl (OH−) ions of the IEM. The H+ and OH− ions may combine in the electrolyte or electrolyte solution to form water. The IEM is typically in the form of porous beads that are formed from crosslinked polymers, such as polystyrene, that are doped or grafted with acidic polymers. An example of an acidic polymer may include poly(2-acrylamido-2-methyl-1-propanesulfonic acid) or polyAMPS. The polyAMPS exchange positively charged salt ions for H+. Another example of an acidic polymer may include poly(acrylamido-N-propyltrimethylammonium chloride) or polyAPTAC. The polyAPTAC exchange negatively charged salt ions for OH−.

The IEM may include a mixture of cation absorbing media and anion absorbing media to form a mixed bed media that simultaneously absorbs both anions and cations. Non-limiting examples of the mixed bed media include Amberlite™ IRN150 and TMD-8. The IEM may be formed from ion exchange resins, zeolites, montmorillonite, bentonites, clay, or soil humus, for example. Ion exchange resins, also known as ion exchange polymers, are insoluble matrices normally in the form of small beads fabricated from an organic polymer substrate. Ion exchange resins may have pores on the surface that trap and release ions. Ion exchange resins can include crosslinked polystyrene, for example. Zeolites are microporous, aluminosilicate minerals. Zeolites have a porous structure that allow cations, such as $Na^+$, $K^+$, $Ca^{2+}$, and $Mg^{2+}$, for example, to be accommodated by the zeolite. Common zeolites include analcime, chabazite, clinoptilolite, heulandite, natrolite, phillipsite, and stilbite, for example. In addition to the above materials, other ion exchange media include activated charcoal, both particulate and in the form of fabrics or non-wovens, for example, and Zorflex®, also known as Chemviron Carbon. Chemviron Carbon may also be known as 100% activated carbon. In an experimental embodiment, a fluid having 0.154 moles/liter of NaCl was passed through the ion exchange layer 118. In the experimental embodiment, the ion exchange layer 118 removed Na+ and CL− ions at a rate of about 0.0026 moles per hour. In some embodiments, the ion exchange layer 118 may have a similar or greater ion removal rate.

In some embodiments, the absorbing layer 120 may be formed from a plurality of dual-layer fibers 300. The dual-layer fibers 300 of the absorbing layer 120 may have the inner core 302 formed from a superabsorbent polymer, such as polyacrylates, polyacrylics, or carboxymethyl cellulose. The outer sheathing 304 may be hydrophilic. In some embodiments, the absorbing layer 120 may be formed from single-layer fibers 200 having an elastic polymer such as an elastane polyurethane with superabsorbent particles disposed therein. In some embodiments, fibers of the absorbing layer 120 may be either woven or non-woven. In some embodiments, the absorbing layer 120 may have a thickness in the range of about 1 mm to about 4 mm. In some embodiments, the single layer fibers 200 and the dual-layer fibers 300 may have a tensile strength of about 40 Newtons (N) per 5 cm length in the direction of the applied force with a tolerance of about +/−15%. In some embodiments, the absorbing layer 120 may permit a flow rate of about 0.83 cubic centimeters/hour.

In some embodiments, the superabsorbent or superabsorbent particles may be formed from a superabsorbent polymer (SAP). Generally, relative to their mass, SAPs can absorb and retain large quantities of liquid, and in particular water. For example, some SAPs may be able to absorb about 500 times its own weight in water, or about 30 to 60 times its own volume in water. The ability of an SAP to absorb water may be based in part on the ionic concentration of the fluid being absorbed. SAPs may be of the type often referred to as "hydrogels," "super-absorbents," or "hydrocolloids." SAPs may be formed into fibers or spheres. Spaces or voids between the fibers or spheres may allow a reduced pressure to be transferred within and through the absorbing layer 120.

SAPs may be formed in several ways, for example, by gel polymerization, solution polymerization, or suspension polymerization. Gel polymerization may involve blending of acrylic acid, water, cross-linking agents, and ultraviolet (UV) initiator chemicals. The blended mixture may be placed into a reactor where the mixture is exposed to UV light to cause crosslinking reactions that form an SAP. The mixture may be dried and shredded before subsequent packaging and/or distribution. Solution polymerization may involve a water-based monomer solution that produces a mass of reactant polymerized gel. The monomer solution may undergo an exothermic reaction that drives the cross-linking of the monomers. Following the crosslinking process, the reactant polymer gel may be chopped, dried, and ground to its final granule size. Suspension polymerization may involve a water-based reactant suspended in a hydrocarbon-based solvent. However, the suspension polymerization process must be tightly controlled and is not often used.

SAPs absorb liquids by bonding with water molecules through hydrogen bonding. Hydrogen bonding involves the interaction of a polar hydrogen atom with an electronegative atom. As a result, SAPs absorb water based on the ability of the hydrogen atoms in each water molecule to bond with the hydrophilic polymers of the SAP having electronegative ionic components. High-absorbing SAPs are formed from ionic crosslinked hydrophilic polymers such as acrylics and acrylamides in the form of salts or free acids. In some embodiments, the absorbing layer 120 may use ionic based SAPs formed from ester salts such as sodium and potassium of acrylic, acrylate, and methacrylate copolymers. In some embodiments, the absorbing layer 120 may retain liquid at a rate greater than about 0.83 cubic centimeters/hour.

In some embodiments, the blocking layer 122 may be formed from a plurality of single-layer fibers 200 formed from a highly hydrophobic polymer such as polyurethane or fluorocarbon. Hydrophobicity may be measured by a surface energy of the material, where a lower surface energy corresponds to a higher hydrophobicity. In some embodiments, the hydrophobic polymer of the single-layer fibers 200 of the blocking layer 122 may be about 25 milliNewtons/meter or less. Generally, the blocking layer 122 may prevent liquid flow through the blocking layer 122 by creating a pressure barrier for liquid movement. For example, the hydrophobic material of the blocking layer 122 may prevent liquid passage where the pressure drawing liquid into and through the blocking layer 122 is less than a water breakthrough pressure of the blocking layer 122. Generally, the water breakthrough pressure of a material increases as the hydrophobicity of the material increases. In some embodiments, the blocking layer 122 may have a water breakthrough pressure greater than about 125 mm Hg negative pressure.

The blocking layer 122 may have a non-woven structure to provide for the manifolding of air and negative pressure over the entire area of the structure. Generally, a non-woven structure may have a porosity or density that permits an air flow for a given pressure; similar to a woven structure. In some embodiments, a non-woven may also be referred to as an open non-woven. In some embodiments, the porosity may be measured by the amount of free volume of the non-woven, that is how much of the structure is not occupied by fibers. For example, the blocking layer 122 may have a free volume of about 85% to about 98%. In some embodiments, the blocking layer 122 may permit about 0.2 to about 1.0 liters/m$^2$/minute/Pa of air flow through the blocking layer 122. In some embodiments, the blocking layer 122 may have a thickness in the range of 0.2 mm and about 0.5 mm, and the single-layer fibers 200 may have a tensile strength of about 40 Newtons (N) per 5 cm length in the direction of the applied force with a tolerance of about +/−15%.

In some embodiments, the odor-absorbing layer 124 may be formed from a plurality of single-layer fibers 200 formed from a highly gas permeable polymer such as a polyurethane or a silicone that contains a dispersion of activated carbon particles. The odor-absorbing layer 124 may also have a non-woven structure to provide for the manifolding of air and negative pressure over the entire area of the structure. In some embodiments, the odor-absorbing layer 124 may have a free volume of about 85% to about 98%. In some embodiments, the odor-absorbing layer 124 may permit about 0.2 to about 1.0 liters/m$^2$/minute/Pa of air flow. In some embodiments, the odor absorbing layer 124 may have a thickness in the range of about 0.2 mm and about 1 mm. In some embodiments, the single-layer fibers 200 may have a tensile strength of about 40 Newtons (N) per 5 cm length in the direction of the applied force with a tolerance of about +/−15%.

In some embodiments, the core 112 may also have a rigid layer 126. The rigid layer 126 may be a plurality of single-layer fibers 200 formed from polyurethane or a high hardness polymer. Generally a high hardness polymer has a hardness rating greater than or equal to about 70 Shore A. In some embodiments, the high hardness polymer may have a hardness rating between about 75 Shore A and about 85 Shore A. In some embodiments, the rigid layer 126 may have a thickness in the range of about 1 mm to about 4 mm. The rigid layer 126 may be disposed adjacent to the contact layer 114 or the odor absorbing layer 124. In some embodiments, the rigid layer 126 may resist rucking, folding, or wrinkling of the core 112. In some embodiments, the rigid layer 126 may increase rigidity between about 25% and about 40% over the core 112 without the rigid layer 126. In some embodiments, the single-layer fibers 200 may have a tensile strength of about 40 Newtons (N) per 5 cm length in the direction of the applied force with a tolerance of about +/−15%.

In some embodiments, the contact layer 114 may form a base of the core 112, and the wicking layer 116 may be stacked adjacent to the contact layer 114. The ion exchange layer 118 may be stacked adjacent to the wicking layer 116, and the absorbing layer 120 may be stacked adjacent to the ion exchange layer 118. The blocking layer 122 may be stacked adjacent to the absorbing layer 120, and the odor-absorbing layer 124 may be placed adjacent to the blocking layer 122 to cap the core 112. As each layer is stacked on the previous layer, the layers may be coupled to each other. For example, the wicking layer 116 may be coupled to the contact layer 114 by adhering, welding, or stitching. Each subsequent layer may be coupled in a similar manner to form the core 112. Generally, each layer will extend the full length and width of the core 112 so that a surface area of each layer is substantially the same.

Referring to FIG. 1, the core 112 may be positioned adjacent to the manifold 110, and the cover 108 may be placed over the core 112 and the manifold 110 to form a sealed therapeutic environment or a sealed space. The negative-pressure source 104 may be fluidly coupled to the sealed space and operated to draw fluid from the tissue site. In some embodiments, the contact layer 114 may be in contact with the manifold 110. In other embodiments, the contact layer 114 may be in direct contact with the tissue site or skin adjacent to the tissue site. The contact layer 114 may function to decrease irritation of the skin in contact with the core 112.

As fluid is drawn from the tissue site by the negative-pressure source 104, fluid may be drawn through the contact layer 114 and into the wicking layer 116. The wicking layer 116 may function to aid in the distribution of fluid across the core 112. In particular, if a portion of the core 112 is blocked, for example by fluid stored in the absorbing layer 120, the wicking layer 116 may provide a pathway for fluid to move around the blockage and further into the core 112. For example, the hydrophilic properties of the single-layer fibers 200 of the wicking layer 116, or the hydrophilic properties of the outer sheathing 304 of the dual-layer fibers 300 of the wicking layer 116 encourage fluid movement through the wicking layer 116.

Fluid may be drawn from the wicking layer 116 into the ion exchange layer 118. As fluid moves through the ion exchange layer 118, salts in the fluids may be removed, decreasing the ionic concentration of the fluids. Fluids may be drawn from the ion exchange layer 118 into the absorbing layer 120, where the fluids may be stored in the superabsorbent polymers of the absorbing layer 120. The combination of the ion exchange layer 118 and the absorbing layer 120 may increase the storage capacity of the core 112 over a core without the ion exchange layer 118.

The blocking layer 122 may operate to prevent any liquids not trapped by the absorbing layer 120 from moving beyond the blocking layer 122 and out of the core 112, thereby limiting the risk of damage to the negative-pressure source 104. For example, the hydrophobic properties of the single-layer fibers 200 of the blocking layer 122 discourage liquid from moving into and through the blocking layer 122. Finally, fluids, mostly gas, may be drawn through the odor absorbing layer 124, where foul odors that may be traveling with the fluids can be absorbed.

Figure 7:
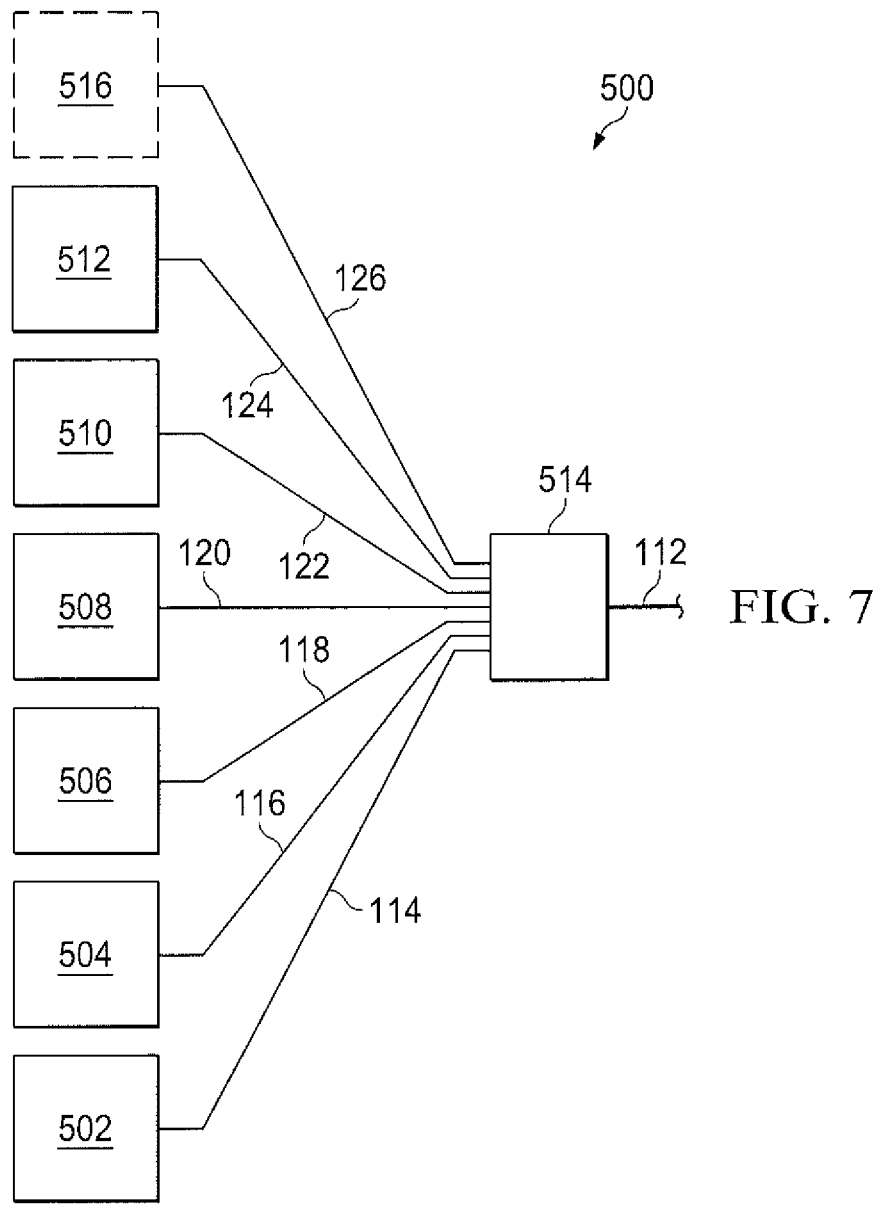
FIG. 7 is a schematic representation of an example embodiment of a manufacturing process for producing the multi-function core of FIG. 6.

FIG. 7 is a schematic diagram, illustrating a manufacturing system 500 for the core 112 that may be associated with some embodiments. The manufacturing system 500 may include a plurality of work stations. In some embodiments, the manufacturing system 500 may have six work stations: a first work station 502, a second work station 504, a third work station 506, a fourth work station 508, a fifth work station 510, and a sixth work station 512. Each work station may be configured to form a separate layer of the core 112. For example, the first work station 502 may be configured to form the contact layer 114, the second work station 504 may be configured to form the wicking layer 116, the third work station 506 may be configured to form the ion exchange layer 118, the fourth work station 508 may be configured to form the absorbing layer 120, the fifth work station 510 may be configured to form the blocking layer 122, and the sixth work station 512 may be configured to form the odor absorbing layer 124.

In some embodiments, each work station 502-512 may form the fibers of the particular layer manufactured by that work station. In some embodiments each work station 502-512 may weave or position the fibers to form the material of the particular layer manufactured by that work station. In some embodiments, each work station 502-512 may both form the fibers of the particular layer and then engage in a process to form the fibers into a particular layer. The layers may then be fed from the work stations 502-512 to an assembly station 514. The assembly station 514 may stack the layers and couple the layers to each other to form a multi-function sheet. Once formed by the assembly station 514, the multi-function sheet may be subdivided into smaller portions, such as individual cores 112, for use with the negative-pressure therapy system 100. For example, in some embodiments, the multi-function sheet may be cut into cores 112 of varying sizes for varying tissue site sizes.

In some embodiments, more or fewer work stations may be used with the manufacturing system 500 to create alternative cores having more or fewer functions. For example, if the core 112 includes the rigid layer 126, the manufacturing system 500 may include a seventh work station 516 configured to manufacture the rigid layer 126. Similarly, if the core 112 does not include the odor absorbing layer 124 or the ion exchange layer 118, the third work station 506 or the sixth work station 512 may be turned off or removed from the manufacturing system 500 entirely.

The systems, apparatuses, and methods described herein may provide significant advantages. For example, the core 112 simplifies dressing assembly as all of the characteristics of a wicking and absorbing core can be provided ready for placement at a tissue site by a clinician or user. A user may only be required to locate the core 112 at the tissue site and attach a cover over the core 112. The core 112 may also resist rucking and the formation of ridges that can result in blisters under the dressing during use. Furthermore, the core 112 is highly configurable during manufacturing, allowing the addition or subtraction of layers and materials to accomplish different functions. For example, antimicrobial agents may be added to the contact layer 114 to aid fighting infection. Similarly, collagen may be added to the contact layer 114 to aid in regulation of matrix metalloproteinase.

While shown in a few illustrative embodiments, a person having ordinary skill in the art will recognize that the systems, apparatuses, and methods described herein are susceptible to various changes and modifications. Moreover, descriptions of various alternatives using terms such as "or" do not require mutual exclusivity unless clearly required by the context, and the indefinite articles "a" or "an" do not limit the subject to a single instance unless clearly required by the context.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described herein may also be combined or replaced by alternative features serving the same, equivalent, or similar purpose without departing from the scope of the invention defined by the appended claims.

What is claimed is:

1. A multi-function core for a dressing, the multi-function core comprising:
   a contact layer configured to be positioned adjacent to a tissue site;
   a wicking layer adjacent to the contact layer;
   an ion exchange layer adjacent to the wicking layer;
   an absorbing layer adjacent to the ion exchange layer;
   a blocking layer adjacent to the absorbing layer; and
   an odor-absorbing layer adjacent to the blocking layer;
   wherein each of the contact layer, the wicking layer, the ion exchange layer, the absorbing layer, the blocking layer, and the odor-absorbing layer are formed from a plurality of fibers disposed in a fibrous web; and
   wherein the plurality of fibers of one or more of the contact layer, the wicking layer, the ion exchange layer, the absorbing layer, the blocking layer, and the odor-absorbing layer comprise dual-layer fibers formed from two materials.

2. The multi-function core of claim 1, wherein one or more of the contact layer, the wicking layer, the ion exchange layer, the absorbing layer, the blocking layer, and the odor-absorbing layer are coextensive.

3. The multi-function core of claim 1, further comprising a rigid layer.

4. The multi-function core of claim 3, wherein the rigid layer is coupled adjacent to the contact layer on a side of the contact layer that is opposite the wicking layer.

5. The multi-function core of claim 3, wherein the rigid layer is adjacent to the odor absorbing layer.

6. The multi-function core of claim 1, wherein the plurality of fibers of one or more of the contact layer, the wicking layer, the ion exchange layer, the absorbing layer, the blocking layer, and the odor-absorbing layer comprise single-layer fibers formed from a single material.

7. The multi-function core of claim 1, wherein the plurality of fibers of one or more of the contact layer, the wicking layer, the ion exchange layer, the absorbing layer, the blocking layer, and the odor-absorbing layer comprise single-layer fibers formed from a single material and dual-layer fibers formed from two materials.

8. The multi-function core of claim 1, wherein the dual-layer fibers comprise an inner core formed from a first material and an outer sheathing formed from a second material.

9. The multi-function core of claim 1, wherein the contact layer, the wicking layer, the ion exchange layer, and the absorbing layer each comprise a plurality of dual-layer fibers, each dual-layer fiber having an inner core formed from a first material and an outer sheathing formed from a second material.

10. The multi-function core of claim 9, wherein the first material of the dual-layer fibers of the contact layer comprises a hydrophobic polyurethane and the second material of the dual-layer fibers of the contact layer comprises a hydrophilic polyurethane.

11. The multi-function core of claim 10, wherein the hydrophilic polyurethane comprises a silicone gel.

12. The multi-function core of claim 9, wherein the first material of the dual-layer fibers of the contact layer comprises an antimicrobial.

13. The multi-function core of claim 9, wherein the second material of the dual-layer fibers of the contact layer comprises an antimicrobial.

14. The multi-function core of claim 12, wherein the antimicrobial is selected from a group consisting of silver and iodine.

15. The multi-function core of claim 9, wherein the first material of the dual-layer fibers of the wicking layer comprises a hydrophobic polyurethane and the second material of the dual-layer fibers of the wicking layer comprises a hydrophilic polyurethane.

16. The multi-function core of claim 9, wherein the first material of the dual-layer fibers of the ion exchange layer comprises a hydrophobic polymer and the second material of the dual-layer fibers of the ion exchange layer comprises a hydrophilic polymer having ion exchange resins disposed therein.

17. The multi-function core of claim 9, wherein the first material of the dual-layer fibers of the absorbing layer comprises a superabsorbent polymer and the second material of the dual-layer fibers of the absorbing layer comprises a hydrophilic polymer.

18. The multi-function core of claim 17, wherein the superabsorbent polymer is selected from a group consisting of: polyacrylates, polyacrylics, and carboxymethyl cellulose.

19. The multi-function core of claim 1, wherein the wicking layer, the ion exchange layer, the absorbing layer, the blocking layer, and the odor-absorbing layer each comprise a plurality of single-layer fibers.

20. The multi-function core of claim 19, wherein the single-layer fibers of the wicking layer are formed from a hydrophilic polymer.

21. The multi-function core of claim 20, wherein the hydrophilic polymer is selected from a group consisting of polyurethane, polyester, and acrylic.

22. The multi-function core of claim 19, wherein the single-layer fibers of the ion exchange layer are formed from a hydrophilic polyurethane having activated carbon particles disposed therein.

23. The multi-function core of claim 19, wherein the single-layer fibers of the absorbing layer are formed from an elastic polymer having superabsorbent polymer disposed therein.

24. The multi-function core of claim 23, wherein the elastic polymer comprises elastane.

25. The multi-function core of claim 23, wherein the superabsorbent polymer comprises superabsorbent fibers.

26. The multi-function core of claim 23, wherein the superabsorbent polymer comprises superabsorbent particles.

27. The multi-function core of claim 19, wherein the single-layer fibers of the blocking layer are formed from a hydrophobic polymer disposed in an open non-woven fibrous web.

28. The multi-function core of claim 27, wherein the hydrophobic polymer comprises a fluorocarbon.

29. The multi-function core of claim 19, wherein the single-layer fibers of the odor-absorbing layer are formed from a gas permeable polymer having activated carbon particles disposed in an open non-woven fibrous web.

30. The multi-function core of claim 29, wherein the gas permeable polymer is selected from a group consisting of polyurethane and silicone.

31. The multi-function core of claim 1, wherein the fibrous web of at least one of the contact layer, the wicking layer, the ion exchange layer, the absorbing layer, the blocking layer, and the odor-absorbing layer comprises a non-woven.

32. The multi-function core of claim 1, wherein the fibrous web of at least one of the contact layer, the wicking layer, the ion exchange layer, the absorbing layer, the blocking layer, and the odor-absorbing layer comprises a woven.

33. The multi-function core of claim 1, wherein one or more of the contact layer, the wicking layer, the ion exchange layer, the absorbing layer, the blocking layer, and the odor-absorbing layer are configured to permit the flow of negative pressure.

34. A multi-function core for a dressing, the multi-function core comprising:
- a contact layer configured to be positioned adjacent to a tissue site;
- a wicking layer adjacent to the contact layer;
- an ion exchange layer adjacent to the wicking layer;
- an absorbing layer adjacent to the ion exchange layer;
- a blocking layer adjacent to the absorbing layer; and
- an odor-absorbing layer adjacent to the blocking layer;
- wherein each of the contact layer, the wicking layer, the ion exchange layer, the absorbing layer, the blocking layer, and the odor-absorbing layer are formed from a plurality of fibers disposed in a fibrous web; and
- wherein the contact layer, the wicking layer, the ion exchange layer, and the absorbing layer each comprise a plurality of dual-layer fibers, each dual-layer fiber having an inner core formed from a first material and an outer sheathing formed from a second material.

* * * * *